US010485441B2

(12) United States Patent
Sullivan

(10) Patent No.: US 10,485,441 B2
(45) Date of Patent: Nov. 26, 2019

(54) ANALYZING ECG DATA IN DECIDING ON PATIENT CHEST COMPRESSION TREATMENT

(71) Applicant: PHYSIO-CONTROL, INC., Redmond, WA (US)

(72) Inventor: Joseph L. Sullivan, Kirkland, WA (US)

(73) Assignee: PHYSIO-CONTROL, INC., Redmond, WA (US)

( * ) Notice: Subject to any disclaimer, the term of this patent is extended or adjusted under 35 U.S.C. 154(b) by 0 days.

(21) Appl. No.: 15/713,387

(22) Filed: Sep. 22, 2017

(65) Prior Publication Data

US 2018/0256058 A1 Sep. 13, 2018
US 2019/0216351 A9 Jul. 18, 2019

Related U.S. Application Data

(63) Continuation of application No. 12/910,677, filed on Oct. 22, 2010, now Pat. No. 9,770,183, which is a continuation-in-part of application No. 12/572,691, filed on Oct. 2, 2009, now Pat. No. 9,539,434.

(51) Int. Cl.
*A61N 1/39* (2006.01)
*A61B 5/0452* (2006.01)

(52) U.S. Cl.
CPC .......... *A61B 5/0452* (2013.01); *A61N 1/3925* (2013.01)

(58) Field of Classification Search
CPC ............................ A61N 1/3925; A61N 1/0452
USPC .................................................. 607/3–6, 510
See application file for complete search history.

(56) References Cited

U.S. PATENT DOCUMENTS

| 4,296,755 | A | 10/1981 | Judell |
| 5,662,690 | A | 9/1997 | Cole et al. |
| 6,269,267 | B1 | 7/2001 | Bardy et al. |
| 6,334,070 | B1 | 12/2001 | Nova et al. |
| 6,356,785 | B1 | 3/2002 | Snyder et al. |
| 6,553,257 | B2 | 4/2003 | Snyder et al. |
| 7,567,837 | B2 | 7/2009 | Weil et al. |
| 7,580,741 | B2 | 8/2009 | Cazares et al. |
| 7,593,772 | B2 | 9/2009 | Sherman |
| 7,623,915 | B2 | 11/2009 | Sullivan et al. |
| 7,630,762 | B2 | 12/2009 | Sullivan et al. |
| 2004/0162585 | A1 | 8/2004 | Elghazzawi et al. |
| 2004/0267325 | A1 | 12/2004 | Geheb et al. |
| 2005/0137628 | A1 | 6/2005 | Young et al. |
| 2006/0173500 | A1 | 8/2006 | Walker et al. |
| 2006/0173501 | A1 | 8/2006 | Stickney et al. |
| 2007/0213775 | A1 | 9/2007 | Snyder |
| 2007/0219588 | A1 | 9/2007 | Freeman |
| 2008/0027338 | A1 | 1/2008 | Lu et al. |
| 2010/0076510 | A1 | 3/2010 | Lyster |

OTHER PUBLICATIONS

International Search Report and Written Opinion of corresponding PCT/US2009/059371, dated May 7, 2010 (17 pp.).

*Primary Examiner* — Nadia A Mahmood
(74) *Attorney, Agent, or Firm* — Lane Powell PC

(57) ABSTRACT

Medical devices, software and methods are provided, for making a decision as to whether to pause patient chest compression treatment in connection with administering electric shock therapy to the patient. The decision is made depending whether signal spikes identified in the ECG data are determined to be QRS complexes, or merely likely impulsive artifact caused by the chest compressions.

18 Claims, 11 Drawing Sheets

DEFIBRILLATION SCENE

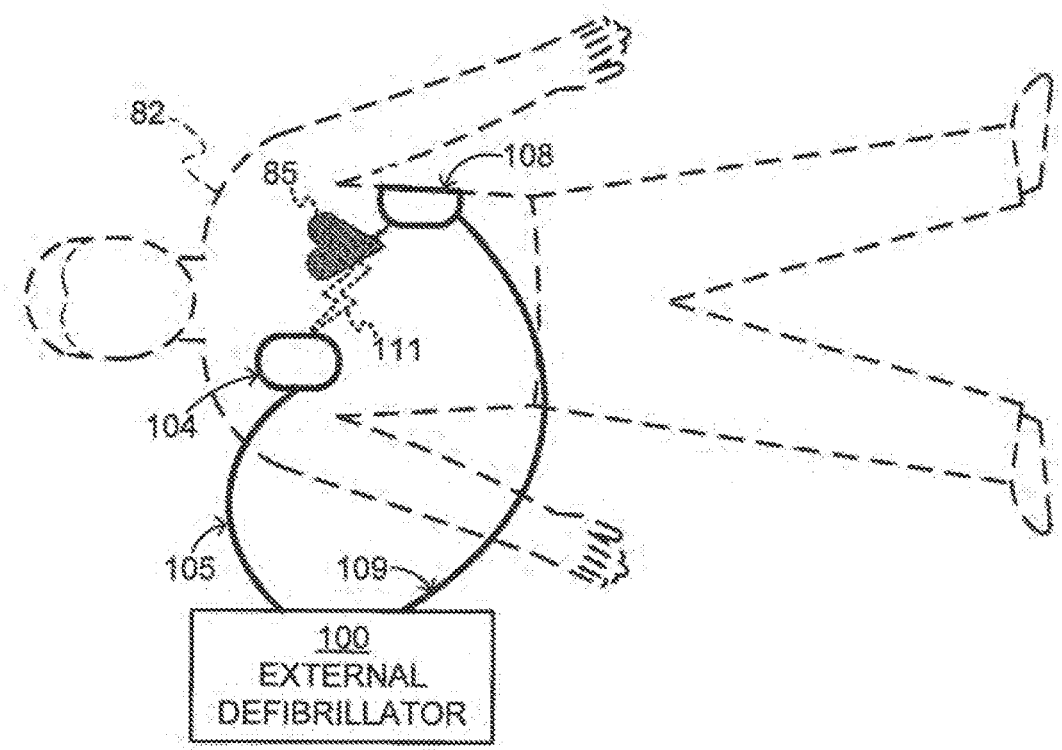
FIG. 1   *DEFIBRILLATION SCENE*
| TYPE OF EXTERNAL DEFIBRILLATOR | INTENDED TO BE USED BY PERSONS: | |
|---|---|---|
| | IN THE MEDICAL PROFESSIONS | NOT IN THE MEDICAL PROFESSIONS |
| DEFIBRILLATOR – MONITOR | √ | |
| AED | √ | √ |
FIG. 2   *TWO MAIN TYPES OF EXTERNAL DEFIBRILLATORS*

COMPONENTS OF EXTERNAL DEFIBRILLATOR

SAMPLE PATIENT ECG DATA

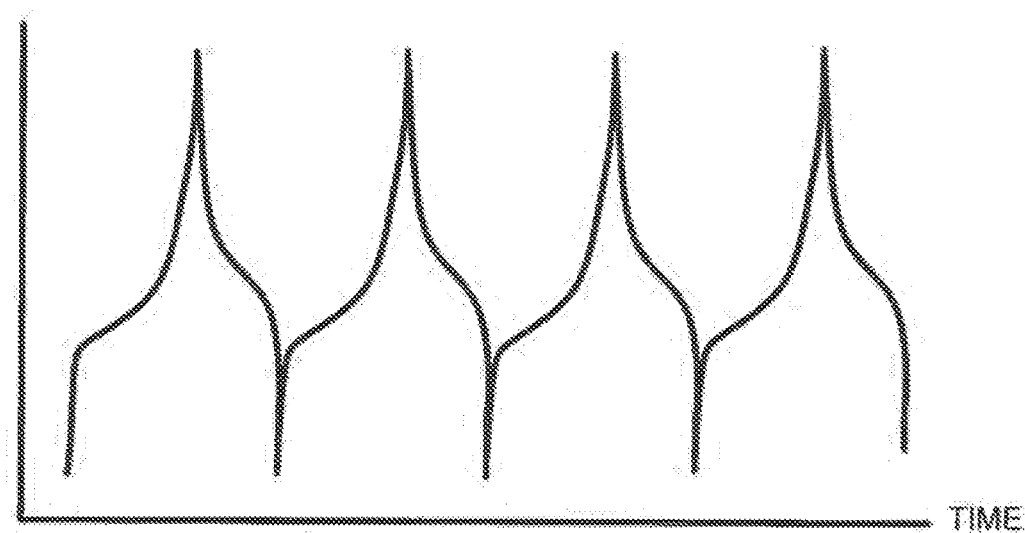
FIG. 6  SAMPLE ECG SIGNAL HAVING IMPULSIVE ARTIFACTS AND NO QRS COMPLEXES
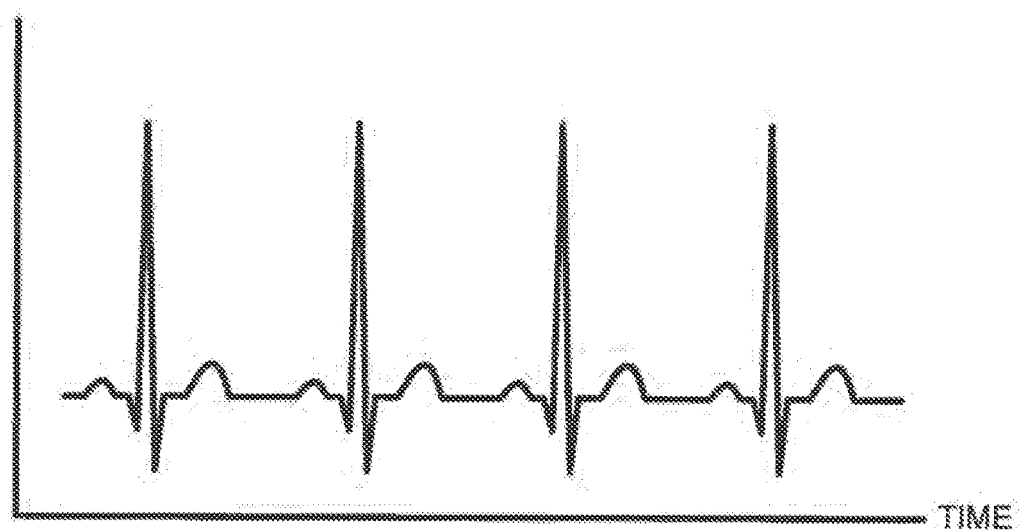
FIG. 7  SAMPLE ECG SIGNAL HAVING QRS COMPLEXES AND NO IMPULSIVE ARTIFACTS SAMPLE POSITIONS OF SIGNAL SPIKES AND SETTING OF WINDOW WITHIN CYCLE INTERVAL FOR ECG DATA HAVING QRS COMPLEXES

ANALYZING ECG DATA IN DECIDING ON PATIENT CHEST COMPRESSION TREATMENT

CROSS-REFERENCE TO RELATED APPLICATION

The preset application is a continuation-in-part of U.S. patent application Ser. No. 12/572,691, filed Oct. 2, 2009, which is hereby incorporated by reference in its entirety.

FIELD

This invention generally relates to deciding on patient chest compression treatment in connection with patient electric shock therapy.

BACKGROUND

In humans, the heart beats to sustain life. In normal operations, it pumps blood through the various parts of the body. More particularly, the various chamber of the heart contract and expand in a periodic and coordinated fashion, which causes the blood to be pumped regularly. More specifically, the right atrium sends deoxygenated blood into the right ventricle. The right ventricle pumps the blood to the lungs, where it becomes oxygenated, and from where it returns to the left atrium. The left atrium pumps the oxygenated blood to the left ventricle. The left ventricle, then, expels the blood, forcing it to circulate to the various parts of the body.

The heart chambers pump because of the heart's electrical control system. More particularly, the sinoatrial (SA) node generates an electrical impulse, which generates further electrical signals. These further signals cause the above-described contractions of the various chambers in the heart, in the right sequence. The electrical pattern created by the sinoatrial (SA) node is called a sinus rhythm.

Sometimes, however, the electrical control system of the heart malfunctions, which can cause the heart to beat irregularly, or not at all. The cardiac rhythm is then generally called an arrhythmia, and some of it may be caused by electrical activity from locations in the heart other than the SA node. Some types of arrhythmia may result in inadequate blood flow, thus reducing the amount of blood pumped to the various parts of the body. Some arrhythmias may even result in a Sudden Cardiac Arrest (SCA). In a SCA, the heart fails to pump blood effectively, and death can occur. In fact, it is estimated that SCA results in more than 250,000 deaths per year in the United States alone. Further, a SCA may result from a condition other than an arrhythmia.

One type of arrhythmia associated with SCA is known as Ventricular Fibrillation (VF). VF is a type of malfunctions where the ventricles make rapid, uncoordinated movements, instead of the normal contractions. When that happens, the heart does not pump enough blood. The person's condition will deteriorate rapidly and, if not reversed in time, they will die soon, e.g. within ten minutes.

Ventricular Fibrillation can often be reversed using a life-saving device called a defibrillator. A defibrillator, if applied properly, can administer an electrical shock to the heart. The shock may terminate the VF, thus giving the heart the opportunity to resume pumping blood. If VF is not terminated, the shock may be repeated, often at escalating energies.

A challenge with defibrillation is that the electrical shock must be administered very soon after the onset of VF. There is not much time: the survival rate of persons suffering from VF decreases by about 10% for each minute the administration of a defibrillation shock is delayed. After about 10 minutes the rate of survival for SCA victims averages less than 2%.

The challenge of defibrillating early after the onset of VF is being met in a number of ways. First, for some people who are considered to be a at a higher risk of VF, an Implantable Cardioverter Defibrillator (ICD) can be implanted surgically. An ICD can monitor the person's heart, and administer an electrical shock as needed. As such, an ICD reduces the need to have the higher-risk person be monitored constantly by medical personnel.

Regardless, VF can occur unpredictably, even so a person who is not considered at risk. As such, VF can be experienced by many people who lack the benefit of ICD therapy. When VF occurs to a person who does not have an ICD, they collapse, because blood flow has stopped. They should receive therapy quickly.

For a VF victim without an ICD, a different type of defibrillator can be used, which is called an external defibrillator. External defibrillators have been made portable, so they can be brought to a potential VF victim quickly enough to revive them.

During VP, the person's condition deteriorates, because the blood is not flowing to be brain, heart, lungs, and other organs. Blood flow must be restored, if resuscitation attempts are to be successful.

Cardiopulmonary Resuscitation (CPR) is one method of forcing blood flow in a person experiencing cardiac arrest. In addition, CPR is the primary recommended treatment for some patients with some kinds of non-VF cardiac arrest, such as asystole and pulseless electrical activity (PEA). CPR is a combination of techniques that include chest compressions to force blood circulation, and rescue breathing to force respiration.

Properly administered CPR provides oxygenated blood to critical organs of a person in cardiac arrest, thereby minimizing the deterioration that would otherwise occur. As such, CPR can be beneficial for persons experiencing VF, because it slows the deterioration that would otherwise occur while a defibrillator is being retrieved. Indeed, for patients with an extended down-time, survival rates are higher if CPR is administered prior to defibrillation.

It is desired to improve patient outcomes, by making improved decisions of when to administer therapy, such as electrical shocks, CPR, pharmaceuticals, etc. Patient outcomes are sometimes analyzed in post-event review.

BRIEF SUMMARY

The present description gives instances of medical devices, software and methods, the use of which may help overcome problems and limitations of the prior art.

In some embodiments, a decision as to whether to pause chest compressions being administered to a patient is made differently, depending on whether signal spikes identified in the ECG data are determined to be QRS complexes or merely likely impulsive artifact caused by the chest compressions.

Embodiments include medical devices such as defibrillators and pacers, and also processors, computers, software, and methods of making the decision.

An advantage over the prior art is that patient outcomes can be improved, especially since impulsive artifacts resembling signal spikes are not misdiagnosed as QRS complexes.

These and other features and advantages of this description will become more readily apparent from the following Detailed Description, which proceeds with reference to the drawings, in which:

BRIEF DESCRIPTION OF THE DRAWINGS

FIG. 1 is a diagram of a scene where an external defibrillator is used to save the life of a person according to embodiments.

FIG. 2 is a table listing two main types of the external defibrillator shown in FIG. 1, and who they might be used by.

FIG. 6 is a time diagram of an ECG signal having impulsive artifacts and no QRS complexes.

FIG. 7 is a time diagram of an ECG signal having QRS complexes an no impulsive artifacts.

DETAILED DESCRIPTION

Figure 3:
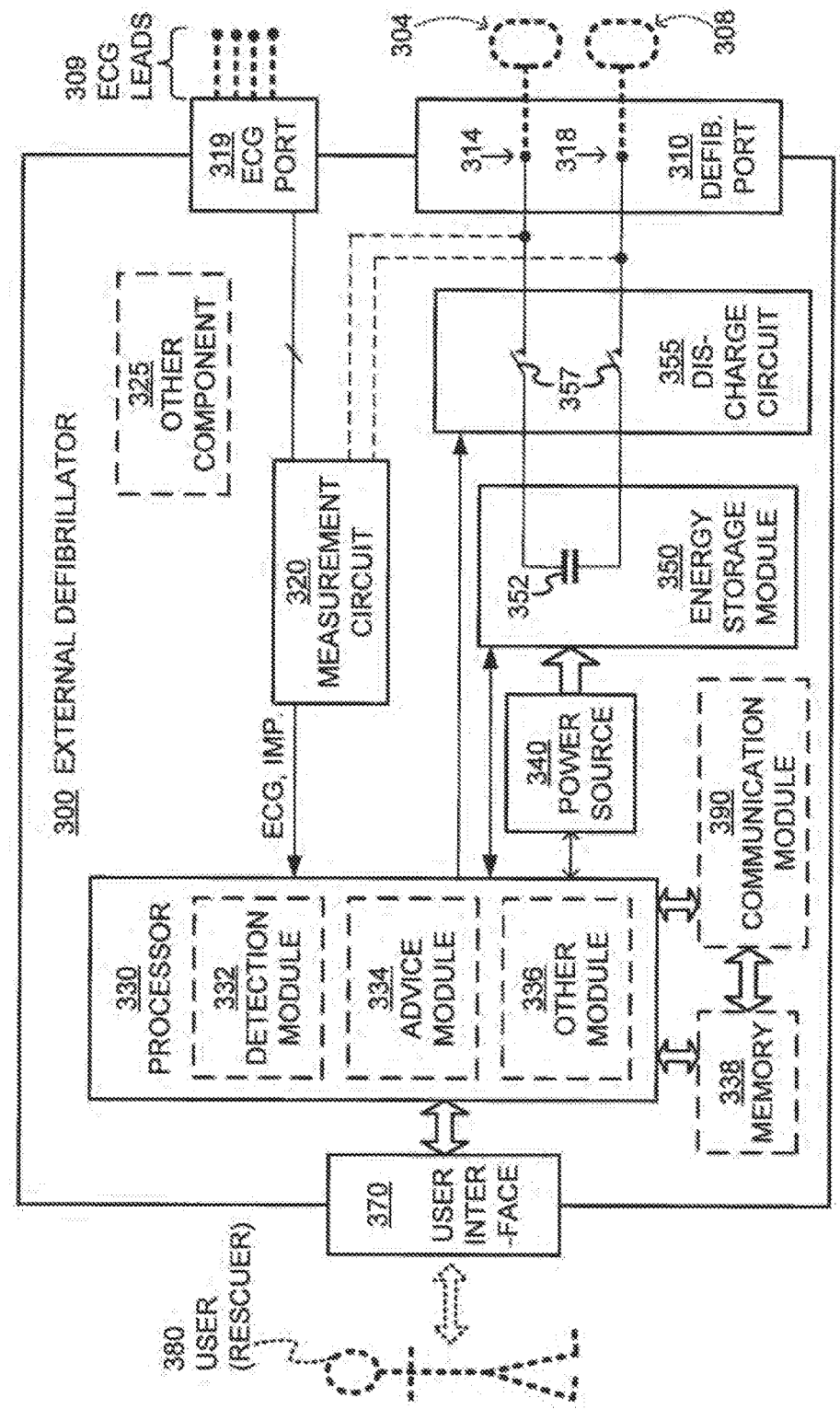
FIG. 3 is a diagram showing components of an external defibrillator, such as the one shown in FIG. 1, which is made according to embodiments.

As has been mentioned, the present description is about making a decision of whether electric therapy should be administered or not. Embodiments include medical devices that can administer electrical therapy, such as defibrillators, pacers, etc. Examples are now described.

FIG. 1 is a diagram of a defibrillation scene. A person 82 is lying on their back. Person 82 could be a patient in a hospital, or someone found unconscious, and then turned to be on their back. Person 82 is experiencing a condition in their heart 85, which could be Ventricular Fibrillation (VF).

A portable external defibrillator 100 has been brought close to person 82. At least two defibrillation electrodes 104, 108 are usually provided with external defibrillator 100, and are sometimes called electrodes 104, 108. Electrodes 104, 108 are coupled with external defibrillator 100 via respective electrode leads 105, 109. A rescuer (now shown) has attached electrodes 104, 108 to the skin of person 82. Defibrillator 100 is administering, via electrodes 104, 108, a brief, strong electric pulse 111 through the body of person 82. Pulses 111, also known as a defibrillation shock, goes also through heart 85, in an attempt to restart it, for saving the life of person 82.

Defibrillator 100 can be one of different types, each with different sets of features and capabilities. The set of capabilities of defibrillator 100 is determined by planning who would use it, and what training they would be likely to have. Examples are now described.

FIG. 2 is a table listing two main types of external defibrillators, and who they are primarily intended to be used by. A first type of defibrillator 100 is generally called a defibrillator-monitor, because it is typically formed as a unit with a patient monitor. A defibrillator-monitor is intended to be used by persons in the medical professions, such as doctors, nurses, paramedics, emergency medical technicians, etc. Such a defibrillator-monitor is intended to be used in a pre-hospital or hospital scenario.

As defibrillator, the device can be one of different varieties, or even versatile enough to be able to switch among different modes that individually correspond to the varieties. One variety is that of an automated defibrillator, which can determine a shock is needed an, if so, charge to a predetermined energy level and instruct the user to administer the shock. Another variety is that of a manual defibrillator, where the user determines the need and controls administering the shock.

As a patient monitor, the device has features additional to what is minimally needed for mere operation as a defibrillator. These features can be for monitoring physiological signals of a person in an emergency scenario. For example, these signals can include a person's full ECG (electrocardiogram) signals. Additionally, these signals can be about the person's temperature, non-invasive blood pressure (NIBP), arterial oxygen saturation/pulse oximetry (SpO2), the concentration of partial pressure of carbon dioxide in the respiratory gases, which is also known as capnography, and so on.

A second type of external defibrillator 100 is generally called and AED, which stands for "Automated External Defibrillator". An AED typically makes the shock/no shock determination by itself, automatically. Indeed, it can sense enough physiological conditions of the person 82 via only the shown defibrillation electrodes 104, 108 of FIG. 1. In its present embodiments, and AED can either administer the shock automatically, or instruct the user to do so, e.g., by pushing a button. Being of a much simpler construction, an AED typically costs much less than a defibrillator-monitor. As such, it makes sense for a hospital, for example, to deploy AEDs at its various floors, in case the more expensive defibrillator-monitor is at an Intensive Care Unit, and so on.

AEDs, however, can also be used by people who are not in the medical profession. More particularly, an AED can be used by many professional first responders, such as policemen, firemen, etc. Even a person with only first-aid training can use one. And AEDs increasingly can supply instructions to whoever is using them.

AEDs are thus particularly useful, because it is so critical to respond quickly, when a person suffers from VF. Indeed, the people who will first reach the VF sufferer may not be in the medical professions.

Increasing awareness has resulted in AEDs being deployed in public or semi-public spaces, so that even a member of the public can use one, if they have obtained first acid and CPR/AED training on their own initiative. This way, defibrillation can be administered soon enough after the onset of VF, to hopefully be effective in rescuing the person.

There are additional types of external defibrillators, which are not listed in FIG. 2. For example, a hybrid defibrillator can have aspects of an AED, and also of a defibrillator-monitor. A usual such aspect is additional ECG monitoring capability.

FIG. 3 is a diagram showing components of an external defibrillator 300 made according to embodiments. These components can be, for example, in external defibrillator 100 of FIG. 1.

External defibrillator 300 is intended for use by a user 380, who would be the rescuer. Defibrillator 300 typically includes a defibrillation port 310, such as a socket. Defibrillation port 310 includes nodes 314, 318. Defibrillation electrodes 304, 308, which can be similar to electrodes 104, 108, can be plugged in defibrillation port 310, so as to make electrical contact with nodes 314, 318, respectively. It is also possible that electrodes can be connected continuously to defibrillation port 310, etc. Either way, defibrillation port 310 can be used for guiding via electrodes to person 82 an electrical charge that has been stored to defibrillator 300, as will be seen later in this document.

If defibrillator 300 is actually a defibrillator-monitor, as was described with reference to FIG. 2, then it will typically also have an ECG port 319, for plugging in ECG leads 309. ECG leads 309 can sense a full ECG signal. Moreover, a defibrillator-monitor could have additional ports (not shown), and an other component 325 for the above described additional features.

Defibrillator 300 also includes a measurement circuit 320. Measurement circuit 320 receives physiological signals from ECG port 319, and also from other ports, if provided. Those physiological signals are sensed, and information about them is rendered by circuit 320 as data, or other signals, etc.

If defibrillator 300 is actually an AED, it may lack ECG port 319. Measurement circuit 320 can obtain physiological signals through nodes 314, 318 instead, when defibrillation electrodes 304, 308 are attached to person 82. In these cases, a person's ECG signal can be sensed as a voltage difference between electrodes 304, 308. Plus, impedance between electrodes 304, 308 can be sensed for detecting, among other things, whether these electrodes 304, 308 have been inadvertently disconnected from the person.

Defibrillator 300 also includes a processor 330. Processor 330 may be implemented in any number of ways. Such ways include, by way of example and not of limitation, digital and/or analog processors such as microprocessors and digital-signal processors (DSPs); controller such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or mora of these, and so on.

Processor 330 can be considered to have a number of modules. One such module can be a detection module 332, which senses outputs of measurement circuit 320. Detection module 332 can include a VF detector. Thus, the person's sensed ECG can be used to determine whether the person is experiencing VF.

Another such module in processor 330 can be an advice module 334, which arrives at advice based on outputs of detection module 332. Advice module 334 can include a Shock Advisory Algorithm, implement decision roles, and so on. The advice can be to shock, to not shock, to administer other forms of therapy, and so on. If the advice is to shock, some external defibrillator embodiments merely report that to the user, and prompt them to do it. Other embodiments further execute the advice, by administering the shock. If the advice is to administer CPR, defibrillator 300 may further issue prompts for it, and so on.

Processor 330 can include additional modules, such as module 336, for other functions. In addition, if other component 325 is indeed provided, it may be operated in part by processor 330, etc.

Defibrillator 300 optionally further includes a memory 338, which can work together with processor 330. Memory 338 may be implemented in any number of ways. Such ways include, by way of example and not of limitation, nonvolatile memories (NVM), read-only memories (ROM), random access memories (RAM), any combination of these, and so on. Memory 338, if provided, can include programs for processor 330, and so on. The programs can be operational for the inherent needs of processor 330, and can also include protocols and ways that decisions can be made by advice module 334. In addition, memory 338 can store prompts for user 380, etc.

Defibrillator 300 may also include a power source 340. To enable portability of defibrillator 300, power source 340 typically includes a battery. Such a battery is typically implemented as a battery pack, which can be rechargeable or not. Sometimes, a combination is used, of rechargeable and non-rechargeable battery packs. Other embodiments of power source 340 can include AC power override, for where AC power will be available, and so on. In some embodiments, power source 340 is controlled by processor 330.

Defibrillator 300 additionally includes an energy storage module 350. Module 350 is where some electrical energy is stored, when preparing it for sudden discharge to administer a shock. Module 350 can be charged from power source 340 to the right amount of energy, as controlled by processor 330. In typical implementations, module 350 includes one or more capacitors 352, and so on.

Defibrillator 300 moreover includes a discharge circuit 335. Circuit 355 can be controlled to permit the energy stored in module 350 to be discharged to nodes 314, 318, and thus also to defibrillation electrodes 304, 308. Circuit 355 can include one or more switches 357. Those can be made in a number of ways, such as by an H-bridge, and so on.

Defibrillator 300 further includes a user interface 370 for user 380. User interface 370 can be made in any number of ways. For example, interface 370 may include a screen, to display what is detected and measured, provide visual feedback to the rescuer for their resuscitation attempts, and so on. Interface 370 may also include a speaker, to issue voice prompts, etc. Interface 370 may additionally include various controls, such as pushbuttons, keyboards, and so on. In addition, discharge circuit 355 can be controlled by processor 350, or directly by user 380 via user interface 370, and so on.

Defibrillator 300 can optionally include other components. For example, a communication module 390 may be provided for communicating with other machines. Such communication can be performed wirelessly, or via wire, or by infrared communication, and so on. This way, data can be communicated, such as patient data, incident information, therapy attempted, CPR performance, and so on.

An additional feature of a defibrillator can be CPR-prompting. Prompts are issued to the user, visual or by sound, so that the user can administer CPR. Examples are taught in U.S. Pat. No. 6,334,070 and U.S. Pat. No. 6,356,785.

Figure 4:
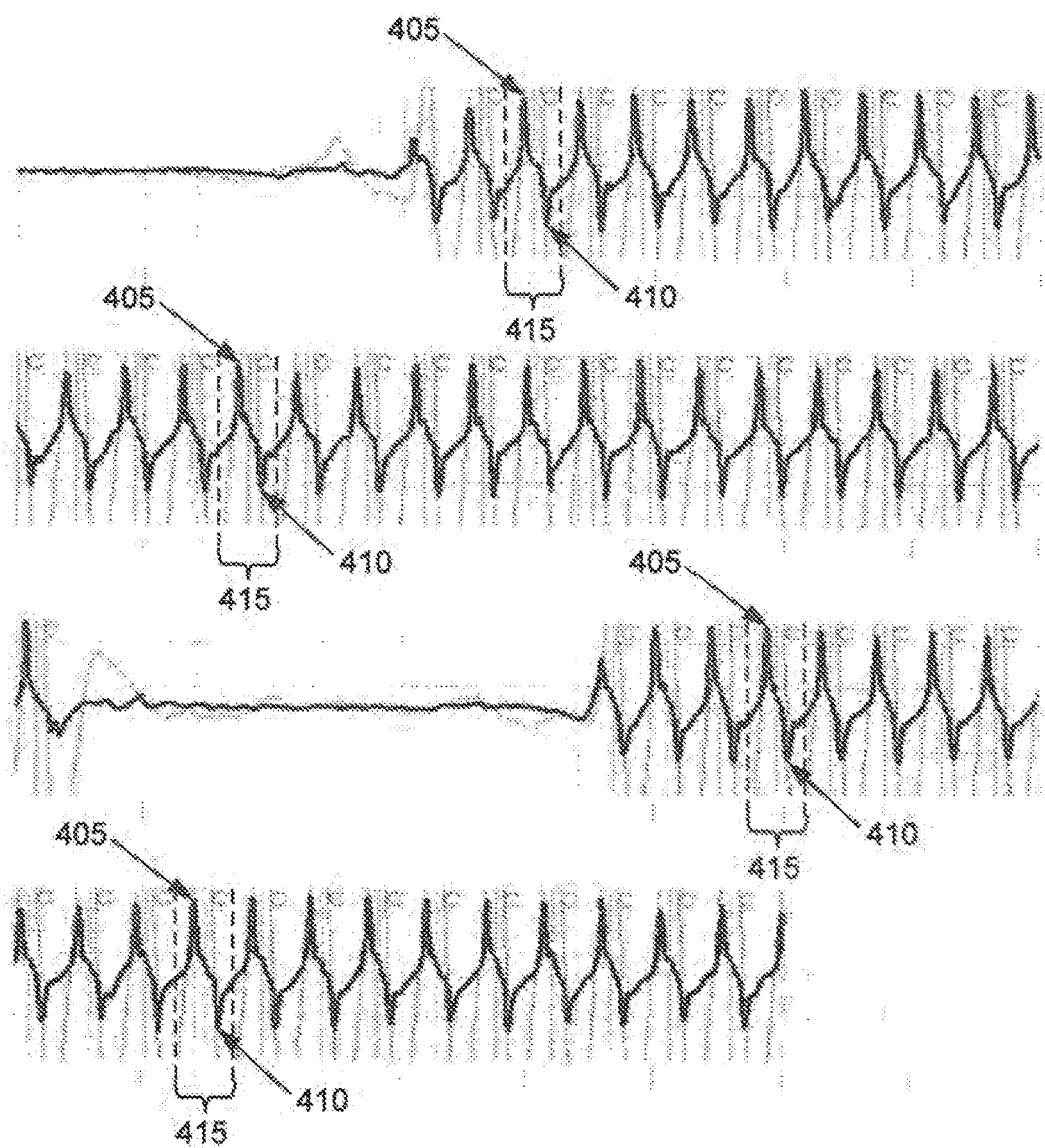
FIGS. 4 and 5 are time diagrams of patient ECG data in the form of signals.
Figure 5:
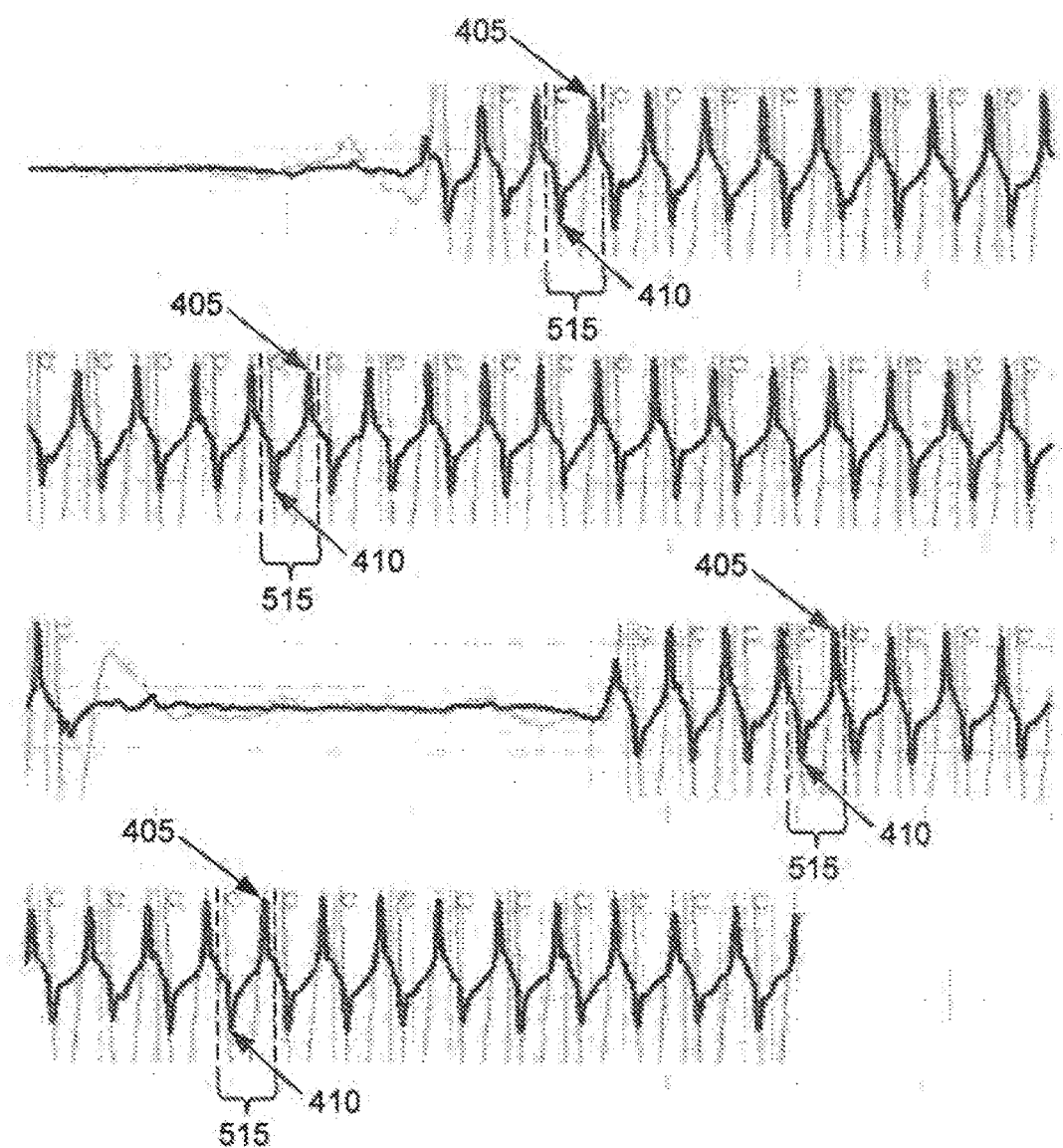

FIGS. 4 and 5 are time diagrams of patient ECG data in the form of signals. The ECG data exhibits an impulsive waveform having signal spikes or peaks that include both positive peaks 405 and negative peaks 410. The time diagrams of FIGS. 4 and 5 also display cycle intervals 415 and 515, respectively, that each correspond to chest compressions that are delivered to the patient.

The cycle intervals 415 illustrated in FIG. 4 are positioned such that each is substantially centered around an identified chest compression. The boundaries of each cycle interval 415 in FIG. 4 are thus each situated substantially midway between site identified chest compression and the next closest chest compression on either side of the identified chest compression.

FIG. 5 shows the same ECG data presented in FIG. 4, including positive peaks 405 and negative peaks 410, but with different cycle intervals 515 that are positioned such that each is situated substantially between two successive identified a chest compressions. Thus, the boundaries of each cycle interval 515 in FIG. 5 are each situated near or at one of the two successive identified chest compression., Because the underlying ECG signal is the same in both FIGS. 4 and 5, the cycle intervals 415 and 515 in FIGS. 4 and 5, respectively, differ only so time relative to the EGG signal. The effects of such a time shift are illustrated below.

FIG. 6 is a time diagram of an ECG signal illustrating example signal spikes that represent impulsive signal artifacts and not QRS complexes. For example, the patient receiving chest compressions may be in a state of asystole such that the signal spikes represent only impulsive artifacts resulting from physical delivery of the chest compressions to the patent. The impulsive artifacts to the ECG signal may have both positive peaks and negative peaks.

FIG. 7 is s time diagram of an ECG signal illustrating example QRS complexes and no impulsive artifacts. The QRS complexes generally include both positive, peaks and negative peaks.

As can be readily discerned by considering the two figures together, there are a number of similarities between the ECG signals of FIGS. 6 and 7. For example, the positive peaks are relatively closer in time to the corresponding negative peaks than to another positive peak. Also, the patient of recurrence is similar. Consequently, current systems often have trouble discerning ECG signals that have impulsive artifacts and no QRS complexes from ECG signals that have QRS complexes and no impulsive artifacts. It follows that such current systems may generate a non-optimal decision regarding patient treatment based on mis-identification, as discussed below.

Figure 8:
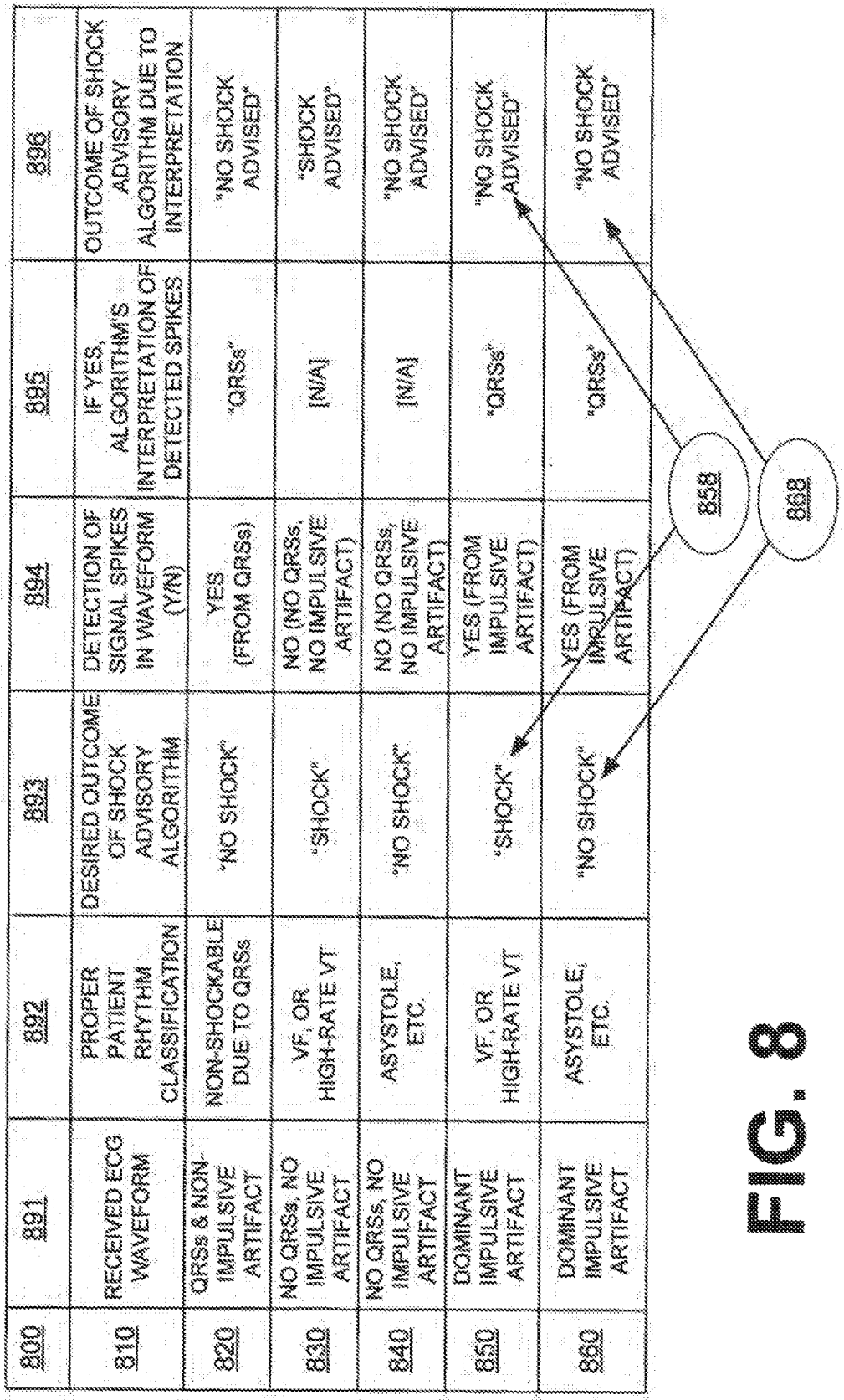
FIG. 8 is a table listing various decisions based on analysis of a detected ECG signal having QRS complexes, impulsive artifacts, or both, and further showing how a device in the prior art might misdiagnose an impulsive artifact as a QRS complex, and not administer a shock where otherwise a shock was needed.

FIG. 8 is a table 800 listing various decisions based on analysis of a detected ECG signal having QRS complexes or impulsive artifacts, and further showing how a device in the prior art might misdiagnose an impulsive artifact as a QRS complex and, as a result, not advise a rescuer to administer a shock in situations where a shock is needed, for example. Impulsive artifacts have been particularly problematic for prior art devices because such devices are unable to distinguish between ECG signals having QRS complexes and VF signals having impulsive artifacts, for example. In addition, an ECG waveform jitter of only a few samples is often enough to result in a prior art device rendering a "no shock" decision in situations where an electric shock should actually be delivered for best patient treatment, as discussed below.

Row 810 of the table 800 provides header information corresponding to each of columns 891-896.

Row 820 pertains to situations in which a received ECG waveform contains QRS signals and non-impulsive artifacts, as indicated at column 891. Column 892 indicates that, in such situations, a proper patient rhythm classification would have the patient be deemed "not shockable" and, therefore, a "no shock" prompt would be the desired outcome of a shock advisory algorithm, as indicated at column 893.

Current systems will identify signal spikes in the received ECG waveform, i.e., due to the presence of the QRS complexes, and properly interpret the signal spikes as corresponding to the QRS complexes, as indicated at columns 894 and 895, respectively. In current systems, the outcome of such a shock advisory algorithm due to the interpretation would be the issuing of a "no shock" prompt to the rescuer, as indicated at column 896.

Rows 830 and 840 pertain to situations in which a received ECG waveform contains nether QRS signals nor impulsive artifacts, as indicated at column 891. In such situations, a proper patient rhythm classification would provide that the patient is experiencing ventricular fibrillation (VF) or high-rate ventricular tachycardia (VT), as indicated at row 830, column 892, or asystole, as indicated at for 840, column 892. If the patient is experiencing VF or high-rate VT, a "shock" prompt would be the desired outcome of a shock advisory algorithm, as indicated at row 830, column 893. If the patient is experiencing asystole, however, a "no shock" prompt would be the desired outcome of such a shock advisory algorithm, as indicated at row 840, column 893.

Current systems will identify no signal spikes in the received ECG waveform, i.e., due to the absence of QRS complexes and impulsive artifacts, as indicated at column 894 for both rows 830 and 840. In current systems, the outcome of such a shock advisory algorithm due to the interpretation would be the issuing of a "shock advised" prompt if the patient is experiencing VF or high-rate VT, as indicated at row 830, column 896, or a "no shock advised" prompt if the patient is experiencing asystole, as indicated at row 840, column 896.

Rows 850 and 860 pertain to situations in which a received ECG waveform contains a dominant impulsive artifact, i.e., resulting from administration of chest compressions to the patient, as indicated at column 891. In such situations, a proper patient rhythm classification would provide that the patient is experiencing VF or high-rate VT, as indicated at row 850, column 892, or asystole, as indicated at row 860, column 892. If the patient is experiencing VF or high-rate VT, a "shock" prompt would be the desired outcome of a shock advisory algorithm, as indicated at row 850, column 893. If the patient is experiencing asystole, however, a "no shock" prompt would be the desired outcome of such a shock advisory algorithm, as indicated at row 860, column 893.

Current systems identify signal spikes in the received ECG waveform, i.e., due to the presence of the dominant impulsive artifact, as indicated at column 894 for both rows 850 and 860. In situations where the patient is experiencing VF or high-rate VT, a shook advisory algorithm of current systems will incorrectly interpret the detected signal spikes as QRS complexes and, therefore, incorrectly issue a "no shock advised" prompt as indicated at row 850, column 895, and row 850, column 896, respectively. Consequently, patients in these situations will not receive the desired outcome, i.e., administration of an electric shock, due to the erroneous interpretation of the signal spikes.

In situations where the patient is experiencing asystole, such a shock advisory algorithm will still incorrectly interpret the detected signal spikes as QRS complexes and thus issue a "no shock advised" prompt, as indicated at row 860, column 895, and row 860, column 896, respectively. While consistent with the desired outcome at row 860, column 893, the "no shock advised" prompt issued at row 860, column 896 is based an the incorrect interpretation of the detected signal spikes as corresponding to QRS complexes when, its actuality, there are no QRS complexes in the received ECG waveform because the patient is experiencing asystole.

The functions of this description may be implemented by one or more devices that include logic circuitry. The device performs functions and/or methods as are described in this document. The logic circuitry may include a processor that may be programmable for a general purpose, or dedicated, such as microcontroller, a microprocessor, a Digital Signal Processor (DSP), etc. For example, the device may be a digital computer like device, such as a general-purpose computer selectively activated or reconfigured by a computer program stored in the computer. Alternately, the device may be implemented by an Application Specific Integrated Circuit (ASIC), etc.

Moreover, methods are described below. The methods and algorithms presented herein are not necessarily inherently associated with any particular computer or other apparatus. Rather, various general-purpose machines may be used with programs in accordance with the teachings herein, or it may prove more convenient to construct more specialized apparatus to perform the required method steps. The required structure for a variety of these machines will become apparent from this description.

In all cases there should be borne in mind the distinction between methods in this description, and the method of operating a comparing machine. This description relates both to methods in general, and also to steps for operating a computer and for processing electrical or other physical signals to generate other desired physical signals.

Programs are additionally included in this description, as are methods of operation of the programs. A program is generally defined as a group of steps leading to a desired result, due to their nature and their sequence. A program is usually advantageously implemented as a program for a computing machine, such as a general-purpose computer, a special purpose computer, a microprocessor, etc.

Storage media are additionally included in this description. Such media, individually or in combination with others, have stored thereon instructions of a program made according to the invention. A storage medium according to the invention is a computer-readable medium, such as a memory, and is read by the computing machine mentioned above.

Performing the steps or instructions of a program requires physical manipulations of physical quantities. Usually, though not necessarily, these quantities may be transferred, combined, compared, and otherwise manipulated or processed according to the instructions, and they may also be stored in a computer-readable medium. These quantities include, for example electrical, magnetic, and electromagnetic signals, and also states of matter that can be queried by such signals. It is convenient at times, principally for reasons of common usage, to refer to these quantities as bits, data bits, samples, values, symbols, characters, images, terms, numbers, or the like. It should be borne in mind, however, that all of these and similar terms are associated with the appropriate physical quantities, and that these terms are merely convenient labels applied to these physical quantities, individually or in groups.

This detailed description is presented largely in terms of flowcharts, display images, algorithms, and symbolic representations of operations of data bits within at least one computer readable medium, such as a memory. Indeed, such descriptions and representations are the type of convenient labels need by those skilled in programming and/or the data processing arts so effectively convey the substance of their work to others skilled in the art. A person skilled in the art of programming may use these descriptions to readily generate specific instructions for implementing a program according to the present invention.

Often, for the sake of convenience only, it is preferred to implement and describe a program as various interconnected distinct software modules or features, individually and collectively also known as software. This is not necessary, however, and there may be cases where modules are equivalently aggregated into a single program with unclear boundaries. In any event, the software modules or features of this description may be implemented by themselves, or in combination with others. Even though it is said that the program may be stored in a computer-readable medium, it should be clear to a person skilled in the art that it need not be a single memory, or even a single machine. Various portions, modules or features of it may reside in separate memories, or even separate machines. The separate machines may be connected directly, or through a network, such as a local access network (LAN), or a global network, such as the Internet.

It will be appreciated that some of these methods may include software steps which may be performed by different modules of art overall software architecture. For example, data forwarding in a router may be performed in a data plane, which consults a local routing table. Collection of performance data may also be performed in a data plane. The performance data may be processed in a control plane, which accordingly may update the local routing table, in addition to neighboring ones. A person skilled in the art will discern which step is best performed in which plane.

An economy is achieved in the present document that a single set of flowcharts is used to describe both programs, and also methods. So, while flowcharts are described in terms of boxes, they can mean both method and programs.

For this description, the methods may be implemented by machine operations. In other words, embodiments of programs are made such that they perform methods of the invention that are described in this document. These may be optionally performed in conjunction with one or more human operators performing some, but not all of them. As per the above, the users need not be collocated with each other, but each only with a machine that houses a portion of the program. Alternately, some of these machines may operate automatically, without users and/or independently from or each other.

Methods are now described.

Figure 9:
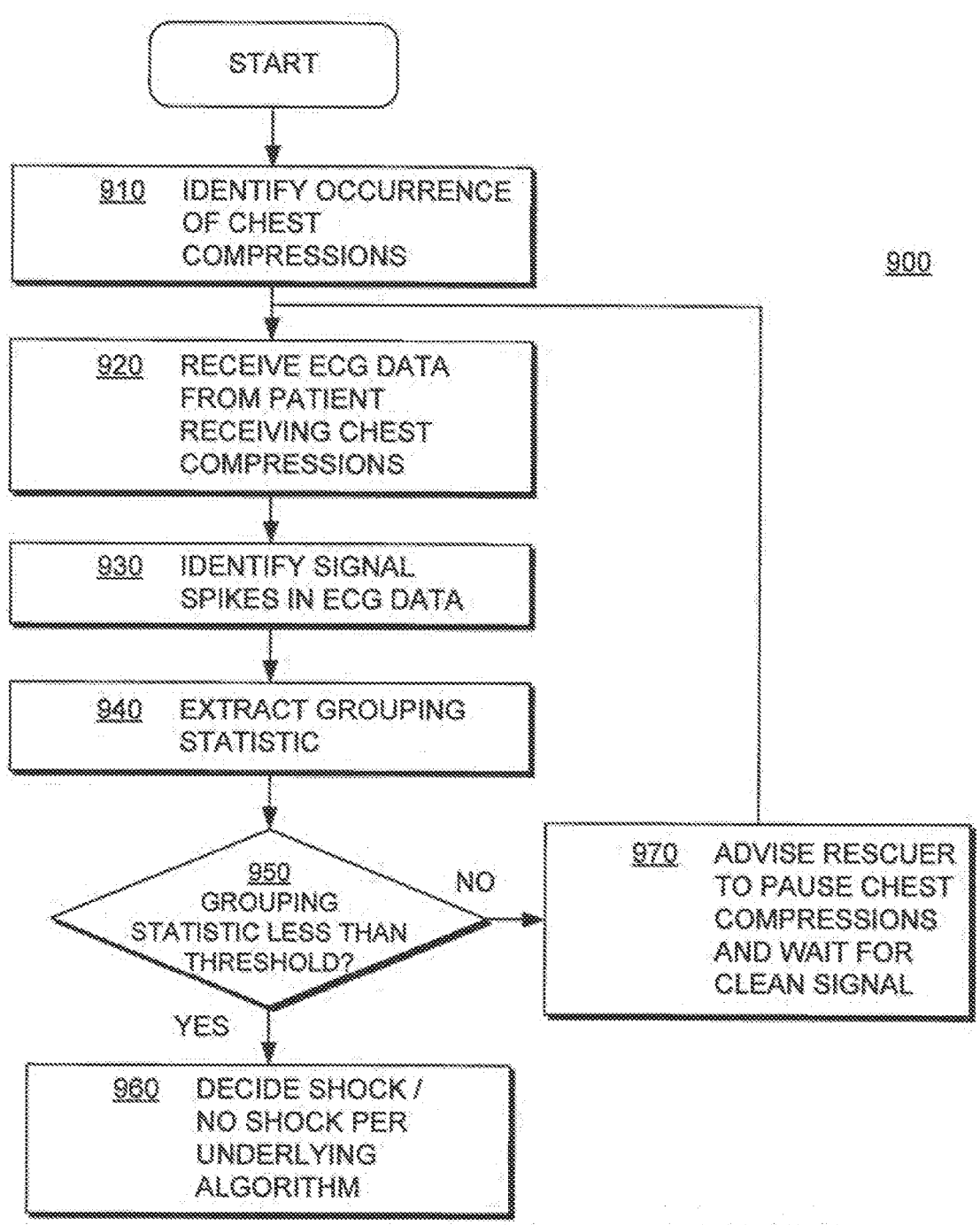
FIGS. 9 and 10 are flowcharts for illustrating methods according to embodiments.
Figure 10:
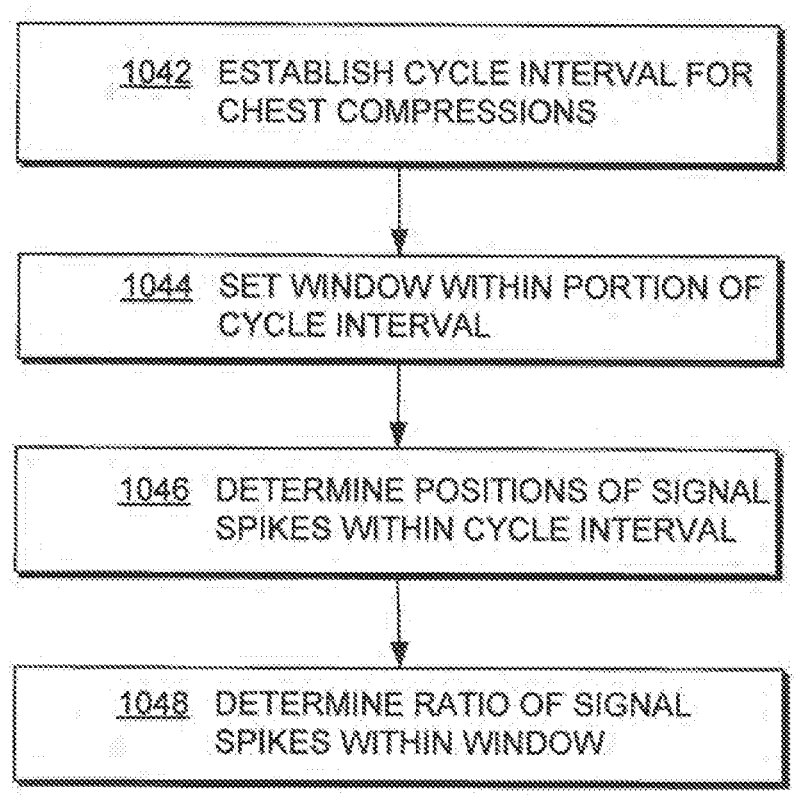

FIGS. 9 and 10 show a flowchart 900 for describing methods according to embodiments. The methods of flowchart 900 may be practiced by systems, devices, and software according to embodiments. For example, the methods illustrated by flowchart 900 can be performed by the processor 330 illustrated in FIG. 3.

Chest compressions may be delivered to a patient by one or both of a rescuer and a chest compression machine controlled by the rescuer. A detection module, such as the detection module 332 illustrated in FIG. 3, may identify the occurrence of chest compressions, as shown at 910. For example, the occurrence of the chest compressions may be identified by one or both of an impedance signal of the patient and an input signal of a chest compression machine. Chest compression markets may be used in connection with a patient's ECG data to identity each chest compression being administered to the patient over a certain period of time. The detection module may also receive ECG data for the patient receiving the chest compressions, as shown at 920.

A module such as the detection module may identify signal spikes in the ECG data, as shown at 930. The module may then extract a grouping statistic about the timing of the signal spikes relative to the occurrence of the identified chest compressions, as shown at 940 and further illustrated by flowchart 1040 of FIG. 10. The grouping statistic is an effort to identify whether the signal spikes are correlated or aligned with each other and/or with the compression cycle. The grouping statistic can be extracted in any number of ways, for example measuring distances, squares of distances, and so on. In certain embodiments, the grouping statistic may include a number of measured distances between an identified chest compression and certain identified signal spikes. For example, the module may generate a sorted list that ranks or orders the signal spikes by the corresponding measured distances. Alternatively, or in addition, the grouping statistic may include information pertaining to measured distances between an identified signal spike and some or all of the other identified signal spikes.

The detection module or another module, such as the advice module 334 or other module 336 illustrated in FIG. 3, may then compare the grouping statistic to a threshold. For example, the advice module 334 may determine whether the grouping statistic is less than a particular threshold, as shown at 950.

Responsive to a first outcome yielded by the comparing, such as a determination at 950 that the grouping statistic is less than the threshold, a module such as the advice module may cause a prompt to be issued for advising the rescuer to either administer or not administer a shock, based on the underlying algorithm, as shown at 960. For example, if the identified signal spikes indicate a condition of VF or high-rate VT, the module may cause a "shock" prompt to be issued for advising the rescuer to administer an electric shock to the patient due to the VF or VT. Alternatively, if the identified signal spikes indicate a condition of asystole, the module may cause a "no shock" prompt to be issued for advising the rescuer to not administer an electric shock to the patient due to the asystole.

Responsive to a second outcome yielded by the comparing, such as a determination at 950 that the grouping statistic is not less than the threshold, the module may cause a prompt to be issued for advising the rescuer to pause the chest compressions and wait for a clean signal, as shown at 970, while returning to 920, regardless of whether the patient is currently experiencing VF, VT, of asystole.

The flowchart 1040 of FIG. 10 describes that a cycle interval is established for the chest compressions being administered to the patient as shown at 1042. The cycle interval may be established by centering an identified chest compression within the cycle interval. In these embodiments, each boundary of the cycle interval is thus situated approximately substantially halfway between the centered chest compression and the next closest chest compression on either side of the centered chest compassion. Alternatively, the module may determine the cycle interval by determining a time distance between two successive identified chest compressions. In these embodiments, the boundaries of the cycle interval will generally correspond to successive identified chest compressions.

A window may be set within a portion of the cycle interval, as shown at 1044. In certain embodiments, the window may be based on a percentage of a width of the cycle interval. In situations where the cycle interval is determined based on a time distance between two successive identified chest compressions, the window may include two non-adjacent sub-windows within the cycle interval. The window may be static or, in certain embodiments, dynamically adjustable. Further, the window may be checked and adjusted after a specified period of time.

Respective positions of at least some of the signal spikes identified within the cycle interval may be determined, as shown at 1046 in FIG. 10 and further illustrated in FIGS. 11 and 12, discussed below. The position of each of the identified signal spikes within the cycle interval may be based on a distance in time between the corresponding signal spike and an identified chest compression. The position of each of the identified signal spikes within the cycle interval may also be determined by determining an absolute peak value of the corresponding signal spike. In certain embodiments, the window may be adjusted after the positioning of each identified signal peak or after a certain number of signal peaks have been positioned within the cycle interval. For example, the width of the window may be dependent upon the number of signal peaks positioned within the cycle interval.

A ratio indicating a percentage of the signal spikes that have a position within the window set at 1044 is determined, as shown at 1048 in FIG. 10 and further illustrated to FIGS. 11 and 12, discussed below. In determining the ratio, a numerical determination is made as to how many of the signal spikes within the cycle interval are further positioned within the window. For example, if seventy-five percent of the signal spikes have a position within the window, the determined ratio would indicate such a percentage. This ratio, or grouping statistic, may then be comparer to a threshold, as shown at 950 of FIG. 9, discussed above. The threshold may be an arbitrary value, such as a fixed percentage of the cycle interval, or it may be calculated in any of a number of different ways. Further, the threshold may be adjusted over time, either manually, automatically, or both.

In certain embodiments, the cycle interval may be scaled, normalized, or both before, during, or after either of establishing the cycle interval at 1042 and positioning the signal spikes within the cycle interval at 1046.

Figure 11:
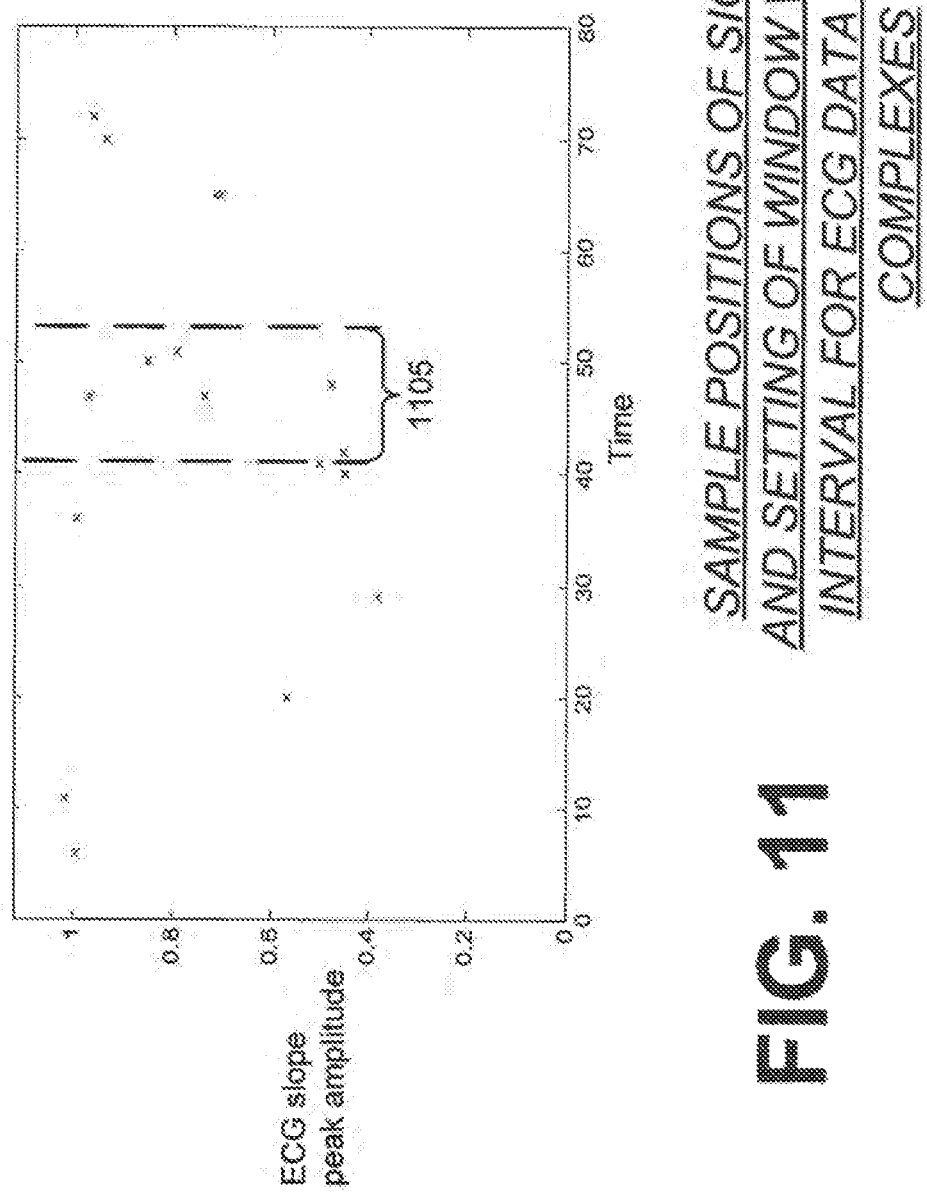
FIGS. 11 and 12 are diagrams for showing the arranging of signal peaks and setting of a window within a cycle interval.
Figure 12:
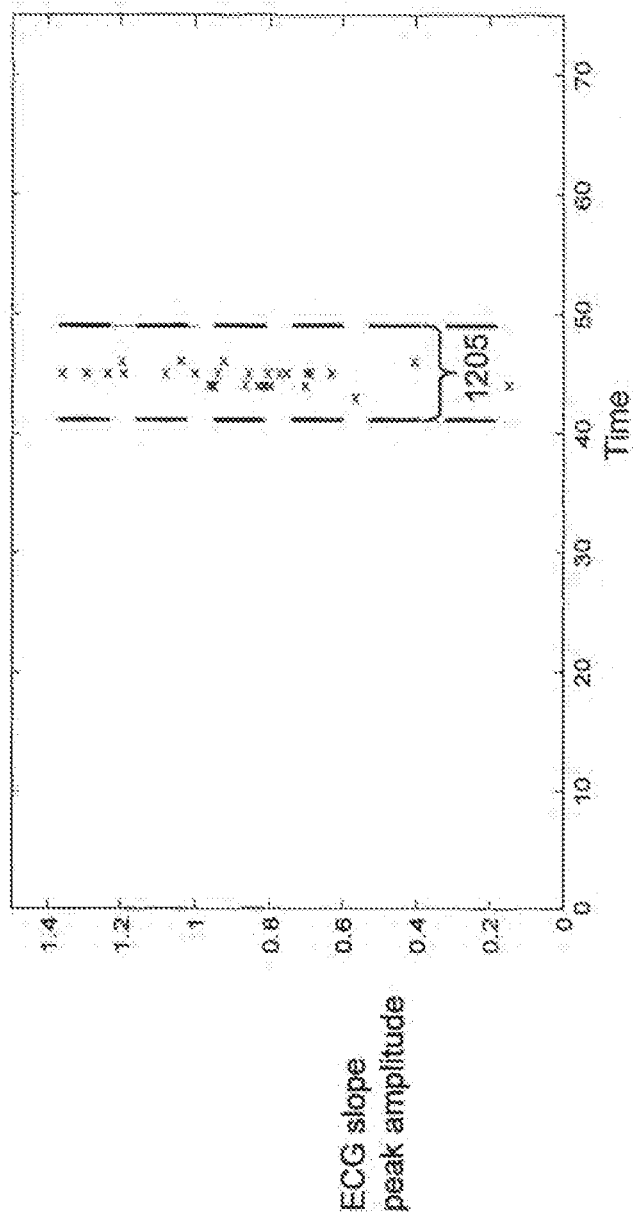

FIGS. 11 and 12 are diagrams for showing the arranging of signal peaks end setting of a window within a cycle interval. The cycle intervals shown in FIGS. 11 and 12 each correspond to a mapping of ECG slope peak amplitude in the y-axis to time its the x-axis. Its other words, for each signal spike in ECG data received from a patient receiving chest compressions, a point is positioned within the cycle interval that corresponds to the value of the signal peak in the y-axis and corresponds to the time of occurrence in the x-axis. In FIGS. 11 and 12, the value of each signal peak is an absolute value, though other embodiments may involve the actual value of the signal peaks. In certain embodiments, the time of occurrence for a point may be relative to a corresponding chest compression, such as the chest compression closest in time to the point. For example, in situations where signal spikes in the ECG signal generally correspond to chest compressions, the corresponding points will generally be positioned in relatively close proximity to each other along the x-axis, and possibly along the y-axis as well, particularly if the rescuer applies chest compressions to the patient in a generally uniform manner.

FIG. 11 illustrates a situation in which the patient ECG data has QRS complexes and no impulsive artifacts. Accordingly, the number of signal spike points positioned outside of the cycle interval window 1105 is significant and may even exceed the number of signal spike points positioned within the cycle interval window 1105. As a result, the ratio of the number of signal spike points positioned within the cycle interval window 1105 to the number of signal spike points not positioned within the cycle interval window 1105 is relatively low, e.g., below a certain threshold. This may happen in such situations because cardiac activity is typically asynchronous to chest compressions. Therefore, signal spike points corresponding to the QRS complexes will generally be positioned at relatively random locations within the cycle interval.

FIG. 12 illustrates a situation in which the patient ECG data has impulsive artifacts and no QRS complexes. Accordingly, the number or signal spike points positioned within the cycle interval window 1205 significantly exceeds the number of signal spike points positioned outside of the cycle interval window 1105, if any. Consequently, the ratio of the number of signal spike peaks positioned within the cycle interval window 1205 to the number of signal spike peaks not positioned within the cycle interval window 1205 is relatively high, e.g., above the threshold. In the example illustrated is FIG. 12, there are in fact no signal spike peaks that are not within the cycle interval window 1205. This may happen in situations where the patient is experiencing asystole during the ECG analysis.

The cycle interval windows 1105 and 1205 illustrated in FIGS. 11 and 12, respectively, may be adjusted. For example, a window may be established before or as soon as one or more signal spike points are positioned within a cycle interval and, once established, the window may be re-sized, re-positioned, etc. Once a certain number of signal spike points have been positioned within the cycle interval, the window may be adjusted accordingly. For example, if a high percentage of the signal spike points are positioned in relatively close proximity to each other, at least in the x-axis, the width of the window may be decreased proportionately. Windows having a smaller width will generally provide greater accuracy than windows having a greater width because the determinations based thereon will have a correspondingly smaller margin of error.

It should be noted that FIGS. 11 and 12 are provided to illustrate visual representations of cycle intervals and cycle interval windows as used and applied herein. In certain embodiments, such data manipulations might not be performed is such a manner that a visual representation thereof is made available to the rescuer or anyone else. Alternatively, certain embodiments may include providing a visual representation of such information to the rescuer at the time of applying chest compressions to the patient or to others at a later time.

Figure 13:
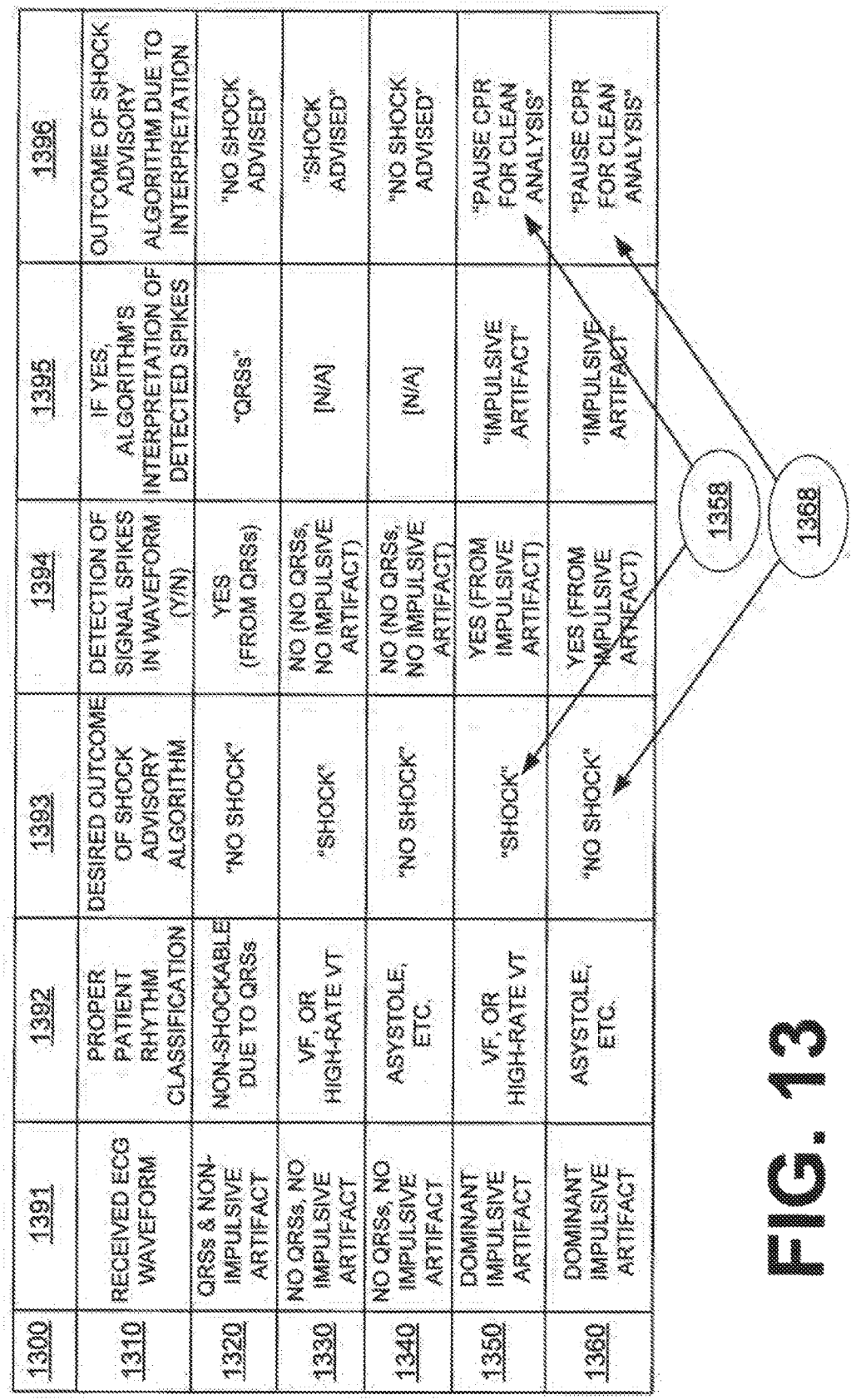
FIG. 13 is a table listing various decisions based on analysis of a detected ECG signal having QRS complexes, impulsive artifacts, or both according embodiments.

FIG. 13 is a table 1300 listing various decisions based on analysis of a detected ECG signal having QRS complexes, impulsive artifacts, or both according to embodiments.

Row 1310 of the table 1300 provides header information corresponding to each of columns 1391-1396.

Row 1320 pertains to situations in which a received ECG waveform contains QRS signals and non-impulsive artifacts, as indicated at column 1391. Column 1392 indicates that, in such situations, a proper patient rhythm classification would have the patient be deemed "not shockable" because of the presence of QRS complexes and, therefore, a "no shock" prompt would be the desired outcome of a shock advisory algorithm, as indicated at column 1393.

According to embodiments, systems will identify signal spikes in the received ECG waveform, i.e., due to the presence of the QRS complexes, and properly interpret the signal spikes as corresponding to the QRS complexes for row 1320, as indicated at columns 1394 and 1395, respectively. The outcome of such a shock advisory algorithm due to the interpretation would be the proper issuing of a "no shock" prompt to the rescuer, as indicated at column 1396.

Rows 1330 and 1340 pertain to situations its which a received ECG waveform contains neither QRS signals nor impulsive artifacts, as indicated at column 1391. In such situations, a proper patient rhythm classification would provide that the patient is experiencing ventricular fibrillation (VF) or high-rate ventricular tachycardia (VT), as indicated at row 1330, column 1392, or asystole, as indicated at row 1340, column 1392. If the patient is experiencing VF or high-rate VT, a "shock" prompt would be the desired outcome of a shock advisory algorithm, as indicated at row 1330, column 1393. If the patient is experiencing asystole, however, a "no shock" prompt would be the desired outcome of such a shock advisory algorithm, as indicated at row 1340, column 1393.

According to embodiments, systems will identify no signal spikes in the received ECG waveform, i.e., due to the absence of QRS complexes and impassive artifacts, as indicated at column 1394 for both rows 1330 and 1340. The outcome of such a shock advisory algorithm due to the interpretation would be the proper issuing of a "shock advised" prompt if the patient is experiencing VF or high-rate VT, as indicated at row 1330, column 1396, or a "no shock advised" prompt if the patient is experiencing asystole, as indicated at row 1340, column 1396.

Rows 1350 and 1360 pertain to situations in which a received ECG waveform contains a dominant impulsive artifact, i.e., resulting from administration of chest compressions to the patient, as indicated at column 1391. In such situations, a proper patient rhythm classification would provide that the patient is experiencing VF or high-rate VT, as indicated at row 1350, column 1392, or asystole, as indicated at row 1360, column 1392. If the patient is experiencing VF or high-rate VT, a "shock" prompt would be the desired outcome of a shock advisory algorithm, as indicated at row 1350, column 1393. If the patient is experiencing asystole, however, a "no shock" prompt would be the desired outcome of such a shock advisory algorithm, as indicated at row 1360, column 1393.

According to embodiments, systems will identify signal spikes in the received ECG waveform, i.e., due to the presence of the dominant impulsive artifact, as indicated at column 1394 for both rows 1350 and 1360. In situations where the patient is experiencing VF or high-rate VT, a shock advisory algorithm according to embodiments will correctly interpret the detected signal spikes as impulsive artifacts and, therefore, properly issue a "pause CPR for clean analysis" prompt, as indicated at row 1350, column 1395, and row 1350, column 1396, respectively. Consequently, patients in these situations will receive the desired outcome, i.e., the rescuer will be directed to pause CPR and to wait for a clean signal. In contrast, there is nothing in the table 800 of FIG. 8 that describes any type of indication provided to a rescuer that the rescuer should wait for a clean signal in such situations.

In situations where the patient is experiencing asystole, a shock advisory algorithm according to embodiments will correctly interpret the defected signal spikes as impulsive artifacts and thus properly issue a "pause CPR for clean analysis" prompt, as indicated at row 1360, column 1395, and row 1360, column 1396, respectively. Consequently, patients in these situations will also receive the desired outcome, i.e., the rescuer will be directed to pause CPR and to wait for a clean signal. In contrast, there is nothing in the table 800 of FIG. 8 that describes any type of indication provided to a rescuer that the rescuer should wait for a clean signal in such situations.

In this description, numerous details have been set forth in order to provide a thorough understanding. In other instances, well-known features have not been described in detail in order to not obscure unnecessarily the description.

A person skilled in the art will be able to practice the present invention in view of this description, which is to be taken as a whole. The specific embodiments as disclosed and illustrated herein are not to be considered in a limiting sense. Indeed, it should be readily apparent to those skilled in the art that what is described herein may be modified in numerous ways. Such ways can include equivalents to what is described herein. In addition, the invention may be practiced in combination with other systems.

The following claims define certain combinations and sub-combinations of elements, features, steps, and/or functions, which are regarded as novel and non-obvious. Additional claims for other combinations and sub-combinations may be preserved in this or a related document.

What is claimed is:

1. A medical device, comprising:
a processor configured to:
receive ECG data of a patient;
identify signal spikes in the ECG data;
determine whether one or more of the identified signal spikes includes a dominant impulsive artifact indicative of a chest compression administered to the patient during cardiopulmonary resuscitation (CPR), the determination based, at least in part, on a timing of the identified signal spikes relative to an occurrence of at least one identified chest compression;
when the the determination yields a dominant impulsive artifact, generate a rescuer prompt to pause administration of CPR and await a clean ECG signal; and
an output configured to output the rescuer prompt.

2. The medical device of claim 1, wherein the processor is further configured to determine an absence of a QRS complex in the ECG data of the patient.

3. The medical device of claim 1, in which
the processor is configured to extract a grouping statistic by:
establishing a cycle interval for the at least one identified chest compression,
setting a window within a portion the cycle interval,
determining respective positions of at least some of the identified signal spikes within the cycle interval, and
in which the grouping statistic is determined from a ratio indicating a ratio of the respective positions within the window.

4. The medical device of claim 3, in which
the cycle interval is established from a time distance between two successive identified chest compressions.

5. The medical device of claim 3, in which
the window is set as a percentage of a width of the cycle interval.

6. The medical device of claim 3, in which
the window comprises two non-adjacent sub-windows within the cycle interval.

7. The medical device of claim 3, in which
one of the respective positions is determined by a distance in time between its corresponding signal spike and a corresponding detected chest compression.

8. The medical device of claim 7, in which
the determined respective position is measured from an absolute peak value of the corresponding signal spike and the corresponding detected chest compression.

9. The medical device of claim 2, wherein the determination of the absence of the QRS complex in the ECG data of the patient occurs before the determination of whether the one or more of the identified signal spikes includes a dominant impulsive artifact indicative of a chest compression administered to the patient during CPR.

10. The medical device of claim 1, wherein the processor is further configured to determine whether the one or more of the identified signal spikes includes a dominant impulsive artifact indicative of the chest compression by identifying the at least one chest compression by one or both of a patient impedance signal or an input signal of a chest compression machine.

11. The medical device of claim 1, wherein the processor is further configured to extract a grouping statistic about a timing of the identified signal spikes relative to the occurrence of the at least one identified chest compression and to determine whether the identified signal spikes are correlated with one or both of each other or with a chest compression cycle.

12. The medical device of claim 11, wherein the grouping statistic includes a number of measured distances between the at least one identified chest compression and the one or more identified signal spikes.

13. A medical device, comprising:
a processor configured to:
receive ECG data of the patient, at least a portion of the ECG data indicative of asystole;
identify signal spikes in the ECG data;
determine whether one or more of the identified signal spikes includes a dominant impulsive artifact indicative of a chest compression administered to the patient during cardiopulmonary resuscitation (CPR), the determination based, at least in part, on a timing of the identified signal spikes relative to an occurrence of at least one identified chest compression;
generate a rescuer prompt to pause administration of CPR and await a clean ECG signal, the rescuer prompt generated based on the received ECG data indicative of asystole and the determination that one or more of the identified signal spikes includes a dominant impulsive artifact; and
an output configured to output the rescuer prompt.

14. The medical device of claim 13, wherein the processor is further configured to determine an absence of a QRS complex in the ECG data of the patient.

15. The medical device of claim 14, wherein the determination of the absence of the QRS complex in the ECG data of the patient occurs before the determination of whether the one or more of the identified signal spikes includes a dominant impulsive artifact indicative of a chest compression administered to the patient during CPR.

16. The medical device of claim 13, wherein the processor is further configured to determine whether the one or more of the identified signal spikes includes a dominant impulsive artifact indicative of the chest compression by identifying the at least one chest compression by one or both of a patient impedance signal or an input signal of a chest compression machine.

17. The medical device of claim 13, wherein the processor is further configured to extract a grouping statistic about a timing of the identified signal spikes relative to the occurrence of the at least one identified chest compression and to determine whether the identified signal spikes are correlated with one or both of each other or with a chest compression cycle.

18. The medical device of claim 17, wherein the grouping statistic includes a number of measured distances between the at least one identified chest compression and the one or more identified signal spikes.

* * * * *